United States Patent
Chen et al.

(10) Patent No.: US 11,992,289 B2
(45) Date of Patent: May 28, 2024

(54) FAST REAL-TIME CARDIAC CINE MRI RECONSTRUCTION WITH RESIDUAL CONVOLUTIONAL RECURRENT NEURAL NETWORK

(71) Applicant: Shanghai United Imaging Intelligence Co., Ltd., Shanghai (CN)

(72) Inventors: Zhang Chen, Cambridge, MA (US); Xiao Chen, Cambridge, MA (US); Shanhui Sun, Cambridge, MA (US); Terrence Chen, Cambridge, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 389 days.

(21) Appl. No.: 17/060,988

(22) Filed: Oct. 1, 2020

(65) Prior Publication Data
US 2021/0165064 A1   Jun. 3, 2021

Related U.S. Application Data
(60) Provisional application No. 62/941,904, filed on Nov. 29, 2019.

(51) Int. Cl.
| | |
|---|---|
| A61B 5/00 | (2006.01) |
| G01R 33/36 | (2006.01) |
| G01R 33/561 | (2006.01) |
| G01R 33/563 | (2006.01) |
| G06N 3/08 | (2023.01) |
| G06N 3/084 | (2023.01) |

(52) U.S. Cl.
CPC .......... *A61B 5/0044* (2013.01); *A61B 5/7264* (2013.01); *G01R 33/3642* (2013.01); *G01R 33/5612* (2013.01); *G01R 33/5615* (2013.01); *G01R 33/56325* (2013.01); *G06N 3/08* (2013.01); *G06N 3/084* (2013.01)

(58) Field of Classification Search
CPC ................ A61B 5/055; G01R 33/3642; G01R 33/56325; G06N 3/08
See application file for complete search history.

(56) References Cited

U.S. PATENT DOCUMENTS
| | | | |
|---|---|---|---|
| 10,521,902 B2* | 12/2019 | Avendi | G06V 10/82 |
| 11,510,587 B2* | 11/2022 | Kristanto | G01R 33/5608 |
| 2007/0096733 A1 | 5/2007 | Arunachalam et al. | |
| 2011/0201944 A1* | 8/2011 | Higgins | A61N 1/37258 607/45 |
| 2015/0374237 A1* | 12/2015 | Hu | A61B 5/7292 600/413 |
| 2018/0108132 A1* | 4/2018 | Flamm | G06T 7/12 |
| 2018/0353139 A1* | 12/2018 | Speier | A61B 5/725 |

(Continued)

FOREIGN PATENT DOCUMENTS
| | | |
|---|---|---|
| CN | 109993809 A | 7/2019 |

OTHER PUBLICATIONS
Chen et al.; "Cardiac Functional Analysis with Cine MRI via Deep Learning Reconstruction"; May 17, 2021.*

(Continued)

*Primary Examiner* — Dixomara Vargas
(74) *Attorney, Agent, or Firm* — Zhong Law LLC (57) ABSTRACT

A method includes using fully sampled retro cine data to train an algorithm, and applying the trained algorithm to real time MR cine data to yield reconstructed MR images.

20 Claims, 5 Drawing Sheets

(56) References Cited

U.S. PATENT DOCUMENTS

| | | | |
|---|---|---|---|
| 2019/0125206 A1* | 5/2019 | Kristanto | G06T 7/174 |
| 2019/0138693 A1* | 5/2019 | Muller | G06N 3/02 |
| 2019/0172230 A1 | 6/2019 | Mailhe et al. | |
| 2019/0266761 A1* | 8/2019 | Malkiel | G01R 33/5611 |
| 2019/0277935 A1* | 9/2019 | Zeng | G06N 3/0454 |
| 2019/0325621 A1* | 10/2019 | Wang | A61B 5/00 |
| 2019/0353741 A1 | 11/2019 | Bolster et al. | |
| 2020/0129780 A1* | 4/2020 | Lachaine | A61N 5/1037 |
| 2020/0375463 A1* | 12/2020 | Hess | A61B 5/7289 |
| 2021/0350179 A1* | 11/2021 | Bello | G06N 3/0454 |
| 2022/0151500 A1* | 5/2022 | Elbaz | G16H 50/50 |
| 2022/0370033 A1* | 11/2022 | Klingensmith | G06T 7/0012 |

OTHER PUBLICATIONS

Alom et al.; Recurrent Residual Convolutional Neural Network Based on U-Net (2U-Net) for Medical Image Segmentation; 2018.*
Qin et al., "Convolutional Recurrent Neural Networks for Dynamic MR Image Reconstruction." IEEE transactions on Medical Imaging 38.1 (2018), 11 pages.

* cited by examiner

FAST REAL-TIME CARDIAC CINE MRI RECONSTRUCTION WITH RESIDUAL CONVOLUTIONAL RECURRENT NEURAL NETWORK

CROSS REFERENCE TO RELATED APPLICATION

This application claims the benefit of U.S. Provisional Application No. 62/941,904, filed 29 Nov. 2019, which is incorporated by reference herein in its entirety.

BACKGROUND

The aspects of the present disclosure relate generally to Magnetic Resonance imaging (MRI), and in particular to using parallel imaging for real time MR cine image reconstruction.

MRI is a widely used medical technique which produces images of a region of interest using magnetic and radio frequency energy. During an MRI scan, volume coils (for example, body coils) and local coils (for example, surface coils) may acquire MR signals produced by nuclear relaxation inside the object being examined. Cardiovascular MRI (cMRI) is the recognized gold standard, that is, a procedure widely recognized as especially effective, for clinical evaluation of cardiac structure and function. Standard CMR applications such as retro-cine rely on ECG gating coupled with several breath-holds to provide high diagnostic image quality. This may present difficulty because a typical patient that may require evaluation of cardiac structure and function may have irregular heartbeat signals and difficulty holding their breath. Real-time cardiac cine MRI utilizes a relatively faster image acquisition and as a result, in contrast to retro-cine MRI, requires neither ECG gating nor breathholding during the data acquisition process. Therefore, real-time cine may be more useful for patients who may have difficulty holding their breath or may have irregular cardiac signals during the MRI examination. However, to achieve the required fast image acquisition speed, real-time cine may generally acquire highly under sampled data (often using more than a 10× acceleration) while utilizing parallel imaging techniques. This may pose computational challenges for MRI image reconstruction in reconstructing the under sampled data and in reconstructing data from the multiple coils used in parallel imaging.

Compressed sensing based approaches have been proposed for real-time cine reconstruction. In addition, several deep learning based approaches have also been proposed for MRI reconstruction. For example, Qin et al. (Qin, Chen, et al. "*Convolutional recurrent neural networks for dynamic MR image reconstruction.*" IEEE transactions on Medical Imaging 38.1 (2018): 280-290) have developed a convolutional recurrent neural network for cardiac MRI image reconstruction. However, those studies have several limitations. In a traditional machine learning or deep learning framework, a golden standard or ground truth data set is required to teach the deep learning model how to reconstruct images. However, acquiring fully sampled real time cine data between heartbeats is nearly impossible given the sampling time and number of coils. As such, the proposed approaches reconstructed simulated under-sampled data from retro-cine data, rather than using actual real-time cine data for evaluation; the acceleration rate was lower than 10×; the previous methods were only designed for single coil image reconstruction rather than multi-coil image reconstruction (i.e., parallel imaging); and the evaluation was performed using only image quality metrics rather than clinical usefulness.

SUMMARY

It would be advantageous to provide a method and system that achieve high quality reconstruction of real-time cardiac cine MRI. The disclosed embodiments are directed to utilizing an algorithm for real-time cardiac cine MR image reconstruction of parallel imaged, under sampled real-time cine data.

According to an aspect of the present disclosure a method includes using fully sampled retro cine data to train an algorithm, and applying the trained algorithm to real time MR cine data to yield reconstructed MR images.

The method may include using one or more of sub-sampled retro-cine data and sub-sampling masks to train the algorithm.

The method may further include using retro cine data from individual coils of a multi-coil MR scanner to train the algorithm.

The real time MR cine data may include real time MR cine data from individual coils of a multiple coil MR scanner.

The fully sampled retro-cine data may be used to calculate loss during training, wherein the loss may include one or more of mean square error loss, L1 loss, Structural Similarity Index (SSIM) loss, or Huber loss.

The algorithm may include a residual convolutional recurrent neural network.

The real time MR cine data may include under-sampled multi-coil real time MR cine data.

The real time MR cine data may include real time MR cine data from individual coils of a multiple coil MR scanner and the algorithm may include a plurality of algorithms, each configured to be applied to data from a different individual coil of the multiple coil MR scanner.

The method may include combining reconstructed images from the plurality of algorithms using a root sum of squares or coil sensitivity maps to generate a final combined image.

The real time MR cine data may include real time MR cine data from individual coils of a multiple coil MR scanner and the algorithm may include a single algorithm configured to be applied to data from the individual coils of the multiple coil MR scanner.

According to another aspect of the present disclosure, a system includes a source of real time MR cine data, and computing circuitry implementing an algorithm trained using fully sampled retro cine data, wherein the trained algorithm is configured to yield reconstructed MR images when applied to real time MR cine data.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings. These embodiments are non-limiting exemplary embodiments, in which like reference numerals represent similar structures throughout the several views of the drawings, wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expressions if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The disclosed embodiments are directed to a method comprising using fully sampled retro cine data to train an algorithm, and applying the trained algorithm to multi-coil real time MRI cine data to yield reconstructed MRI images.

The disclosed embodiments are further directed to a system comprising a source of fully sampled retro cine MR data, an algorithm configured to be trained using the fully sampled retro cine MR data, and a source of multi-coil real time MR cine data, wherein the trained algorithm may be applied to the multi-coil real time MR cine data to yield reconstructed MR images.

Figure 1:
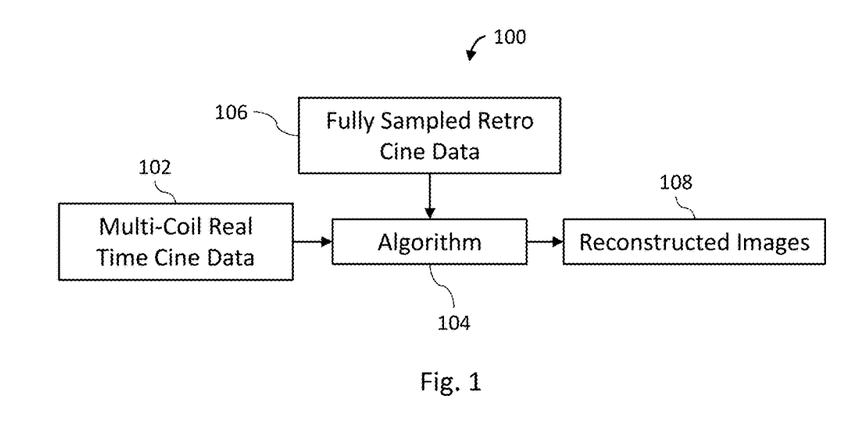
FIG. 1 illustrates an exemplary process flow according to aspects of the disclosed embodiments.

Referring to FIG. 1, a schematic block diagram of an exemplary system 100 incorporating aspects of the disclosed embodiments is illustrated. The system may include a source of multi-coil real time MR cine data 102, an algorithm 104, and a source of fully sampled retro cine MR data 106. The fully sampled retro cine data 106 may be used to train the algorithm 104, and the trained algorithm 104 may be applied to the multi-coil real time MR cine data 102 to yield reconstructed MR images 108.

Figure 2:
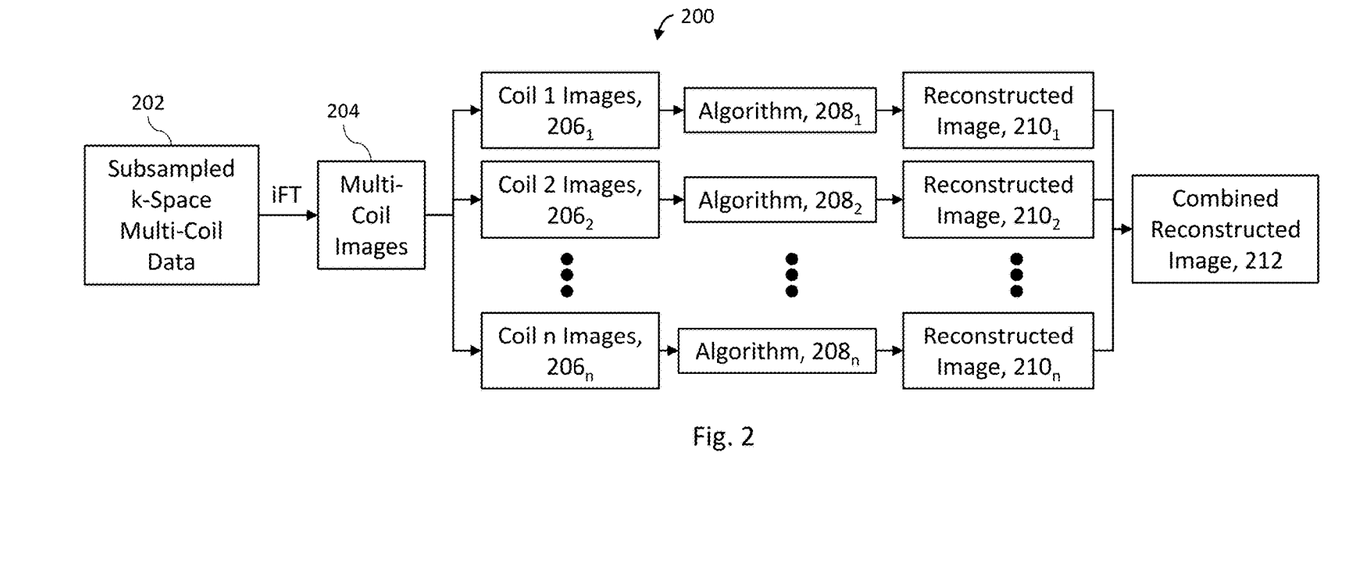
FIG. 2 illustrates an embodiment of an exemplary system incorporating aspects of the disclosed embodiments.
Figure 3:
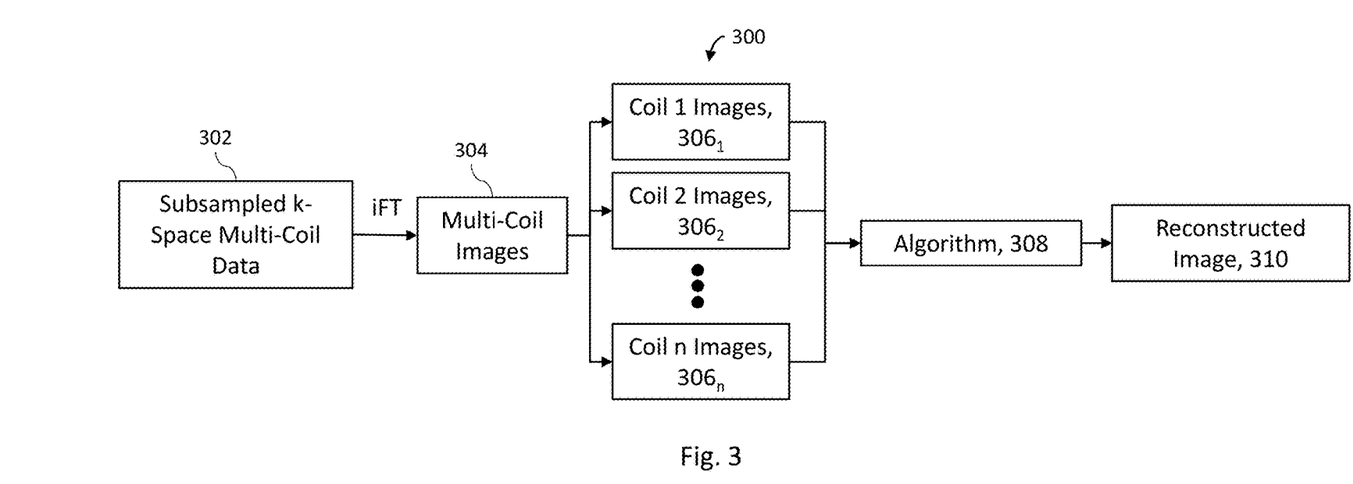
FIG. 3 illustrates an embodiment of another exemplary system incorporating aspects of the disclosed embodiments.

FIGS. 2 and 3 illustrate embodiments of exemplary systems 200, 300 incorporating aspects of the disclosed embodiments. FIG. 2 illustrates an exemplary embodiment that provides independent multi-coil reconstruction by providing an algorithm in the form of a deep learning model for each coil of a multi-coil MR system. An inverse Fourier transform (iFT) may be performed on subsampled k-space real time multi-coil data 202 to yield multi-coil images 204 that include aliasing and artifacts due to the subsampling. The images 204 with aliasing and artifacts may be separated into individual images $206_1$-$206_n$ according to the individual coils from which they are obtained. An associated algorithm $208_1$-$208_n$ may be applied to each image $206_1$-$206_n$ to yield a corresponding reconstructed image $210_1$-$210_n$ and the reconstructed images $210_1$-$210_n$ may be combined to yield a combined reconstructed image 212. The reconstructed images from each individual coil may be combined using root sum of square (RSS) or coil sensitivity maps to generate the final combined reconstructed image 212.

FIG. 3 illustrates an exemplary embodiment that provides parallel multi-coil reconstruction by applying a single algorithm to images from the coils. An inverse Fourier transform (iFT) may be performed on subsampled k-space real time multi-coil data 302 to yield multi-coil images 304 that include aliasing and artifacts due to the subsampling. The images 304 with aliasing and artifacts may be separated into individual images $306_1$-$306_n$ according to the individual coils from which they are obtained. The images $306_1$-$306_n$ may be provided as input to a single algorithm 308 to yield a reconstructed image 310.

Figure 4:
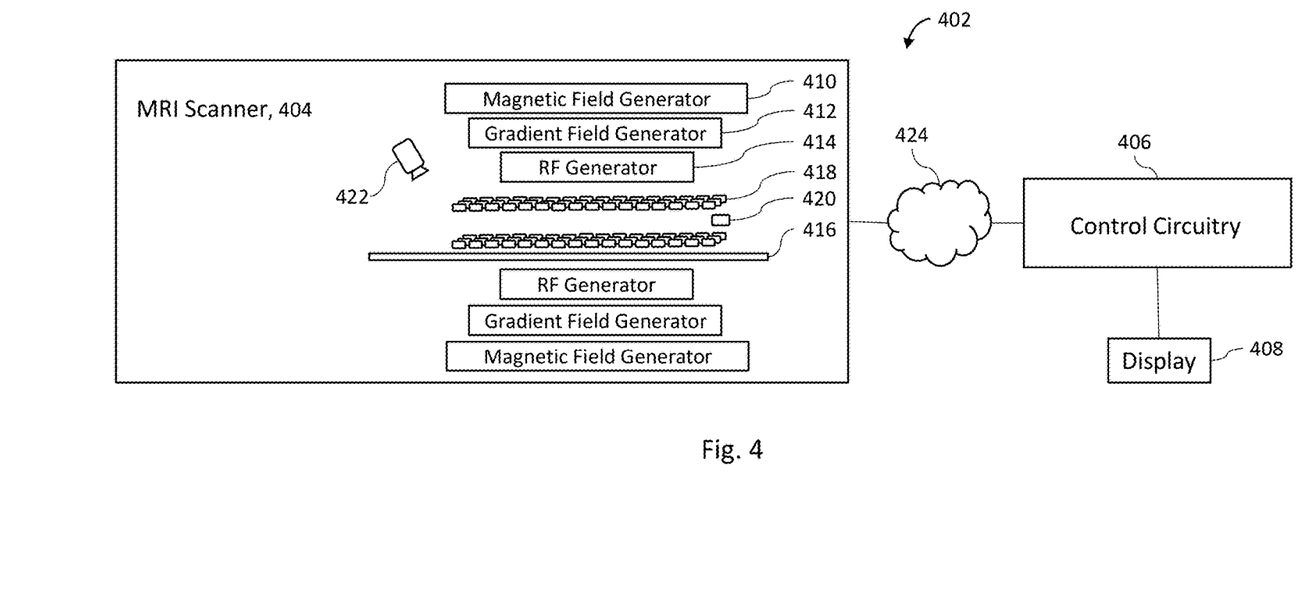
FIG. 4 shows a schematic block diagram of an exemplary multi-coil MRI data source according to the disclosed embodiments.

FIG. 4 shows a schematic block diagram of an exemplary multi-coil MRI data source in the form of an MRI apparatus 402 for providing multi-coil MRI data according to the disclosed embodiments. The MRI apparatus 402 may include an MRI scanner 404, control circuitry 406 and a display 408. The function, size, type, geometry, position, amount, or magnitude of the MRI scanner 404 may be determined or changed according to one or more specific conditions. For example, the MRI scanner 404 may be designed to surround a subject (or a region of the subject) to form a tunnel type MRI scanner, referred to as a closed bore MRI scanner, or an open MRI scanner, referred to as an open-bore MRI scanner. As another example, the MRI scanner may be portable and transportable down hallways and through doorways to a patient, providing MR scanning services to the patient as opposed to transporting the patient to the MRI scanner. In some examples, a portable MRI scanner may be configured to scan a region of interest of a subject, for example, the subject's brain, spinal cord, limbs, heart, blood vessels, and internal organs.

The MRI scanner 404 may include, as shown in cross section in FIG. 4, a magnetic field generator 410, a gradient magnetic field generator 412, and a Radio Frequency (RF) generator 414, all surrounding a table 416 on which subjects under study may be positioned. The MRI scanner 404 may also include one or more coil arrays 418, an ECG signal sensor 420 for capturing MRI data in the form of ECG signals from the subject under study during MRI scanning, and a camera 422 for capturing MRI data in the form of video images of the subject under study during MRI scanning.

In some embodiments, the MRI scanner 404 may perform a scan on a subject or a region of the subject. The subject may be, for example, a human body or other animal body. In some embodiments, the subject may be a patient. The region of the subject may include part of the subject. For example, the region of the subject may include a tissue of the patient. The tissue may include, for example, lung, prostate, breast, colon, rectum, bladder, ovary, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the scan may be a pre-scan for calibrating an imaging scan. In some embodiments, the scan may be an imaging scan for generating an image.

The main magnetic field generator 410 may create a static magnetic field $B_0$ and may include, for example, a permanent magnet, a superconducting electromagnet, a resistive electromagnet, or any magnetic field generation device suitable for generating a static magnetic field. The gradient magnet field generator 412 may use coils to generate a magnetic field in the same direction as $B_0$ but with a gradient in one or more directions, for example, along X, Y, or Z axes in a coordinate system of the MRI scanner 404.

In some embodiments, the RF generator 414 may use RF coils to transmit RF energy through the subject, or region of interest of the subject, to induce electrical signals in the region of interest. The resulting RF field is typically referred to as the Bi field and combines with the $B_0$ field to generate MR signals that are spatially localized and encoded by the gradient magnetic field. The coil arrays 418 may generally operate to sense the RF field and convey a corresponding output to the control circuitry 406. In some embodiments, the coil arrays may operate to both transmit and receive RF energy, while in other embodiments, the coil arrays may operate as receive only.

Figure 5A:
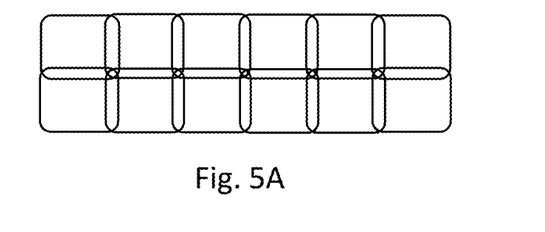
FIGS. 5A and 5B illustrate different MRI multi-coil arrangements according to the disclosed embodiments.
Figure 5B:
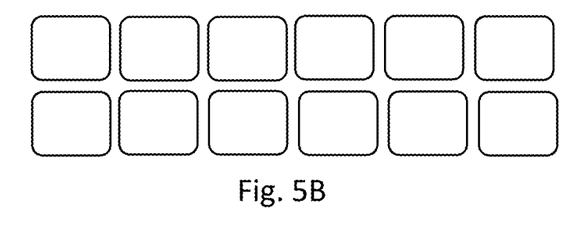

FIGS. 5A and 5B illustrate different MRI multi-coil arrangements. The multi-coil arrangements may include phased array coil arrangements and parallel array coil arrangements. FIG. 5A shows an exemplary phased array coil arrangement where the coils overlap and are coupled together to enhance gain and signal to noise properties. FIG. 5B shows an exemplary parallel array arrangement where the coils are decoupled and optimized for parallel imaging. The coil arrangements may include any number of coils, depending on a particular application. Exemplary numbers of coils may include 12, 16, 24, 32, 64 or more.

Returning to FIG. 4, the control circuitry 406 may control overall operations of the MRI scanner 404, in particular, the magnetic field generator 410, the gradient magnetic field generator 412, the RF generator 414, and the coil arrays 418. For example, the control circuitry 406 may control the magnet field gradient generator to produce gradient fields along one or more of the X, Y, and Z axes, and the RF generator to generate the RF field. In some embodiments, the control circuitry 406 may receive commands from, for example, a user or another system, and control the magnetic field generator 410, the gradient magnetic field generator 412, the RF generator 414, and the coil arrays 418 accordingly.

The control circuitry 406 may be connected to the MRI scanner 404 through a network 424. The network 424 may include any suitable network that can facilitate the exchange of information and/or data for the MRI scanner 404. The network 424 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 424 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 424 may include one or more network access points. For example, the network 424 may include wired and/or wireless network access points such as base stations and/or internet exchange points through which one or more components of the MRI scanner 402 may be connected with the network 424 to exchange data and/or information.

According to some embodiments, the algorithm may be implemented in computing circuitry of the control circuitry 406, while in other embodiments, the algorithm may be implemented in computing circuitry located remotely from the control circuitry 406.

Figure 6:
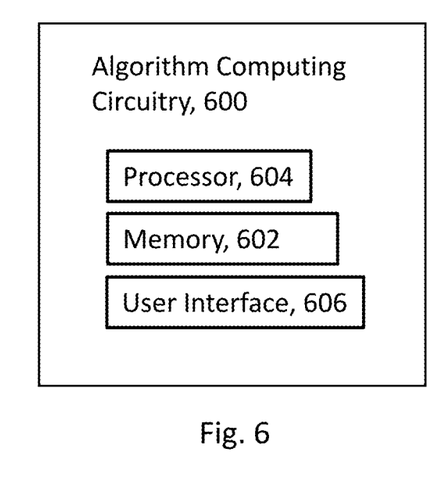
FIG. 6 illustrates an exemplary architecture of computing circuitry in which an algorithm may be implemented according to the disclosed embodiments.

FIG. 6 illustrates an exemplary architecture of the computing circuitry 600 according to the disclosed embodiments. The computing circuitry 600 may include computer readable program code stored on at least one computer readable medium 602 for carrying out and executing the process steps described herein. The computer readable program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The computer readable program code may execute entirely on the computing circuitry 600, partly on the computing circuitry 600, as a stand-alone software package, partly on the computing circuitry 600 and partly on a remote computer or server or entirely on the remote computer or server. In the latter scenario, the remote computer may be connected to the computing circuitry 600 through any type of network, including those mentioned above with respect to network 424.

The computer readable medium 602 may be a memory of the computing circuitry 600. In alternate aspects, the computer readable program code may be stored in a memory external to, or remote from, the computing circuitry 600. The memory may include magnetic media, semiconductor media, optical media, or any media which is readable and executable by a computer. The computing circuitry 600 may also include a computer processor 604 for executing the computer readable program code stored on the at least one computer readable medium 602. In some embodiments, the computer processor may be a graphics processing unit, or graphical processing unit (GPU). In at least one aspect, the computing circuitry 600 may include one or more input or output devices, generally referred to as a user interface 606 which may operate to allow input to the computing circuitry 600 or to provide output from the computing circuitry 600, respectively. The computing circuitry 600 may be implemented in hardware, software or a combination of hardware and software.

Figure 7:
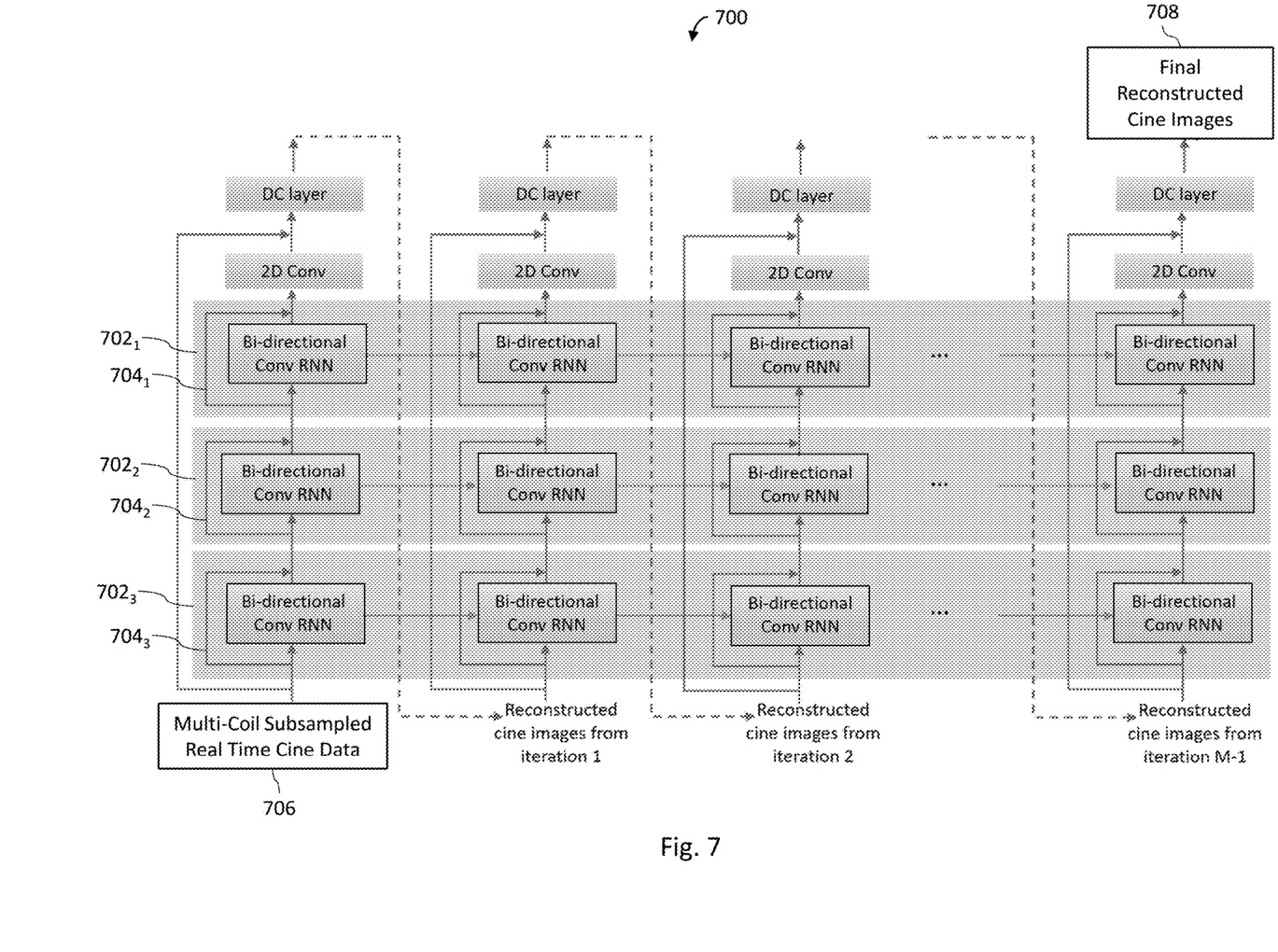
FIG. 7 illustrates an example of an algorithm in the form of a deep residual convolutional recurrent neural network.
Figure 8:
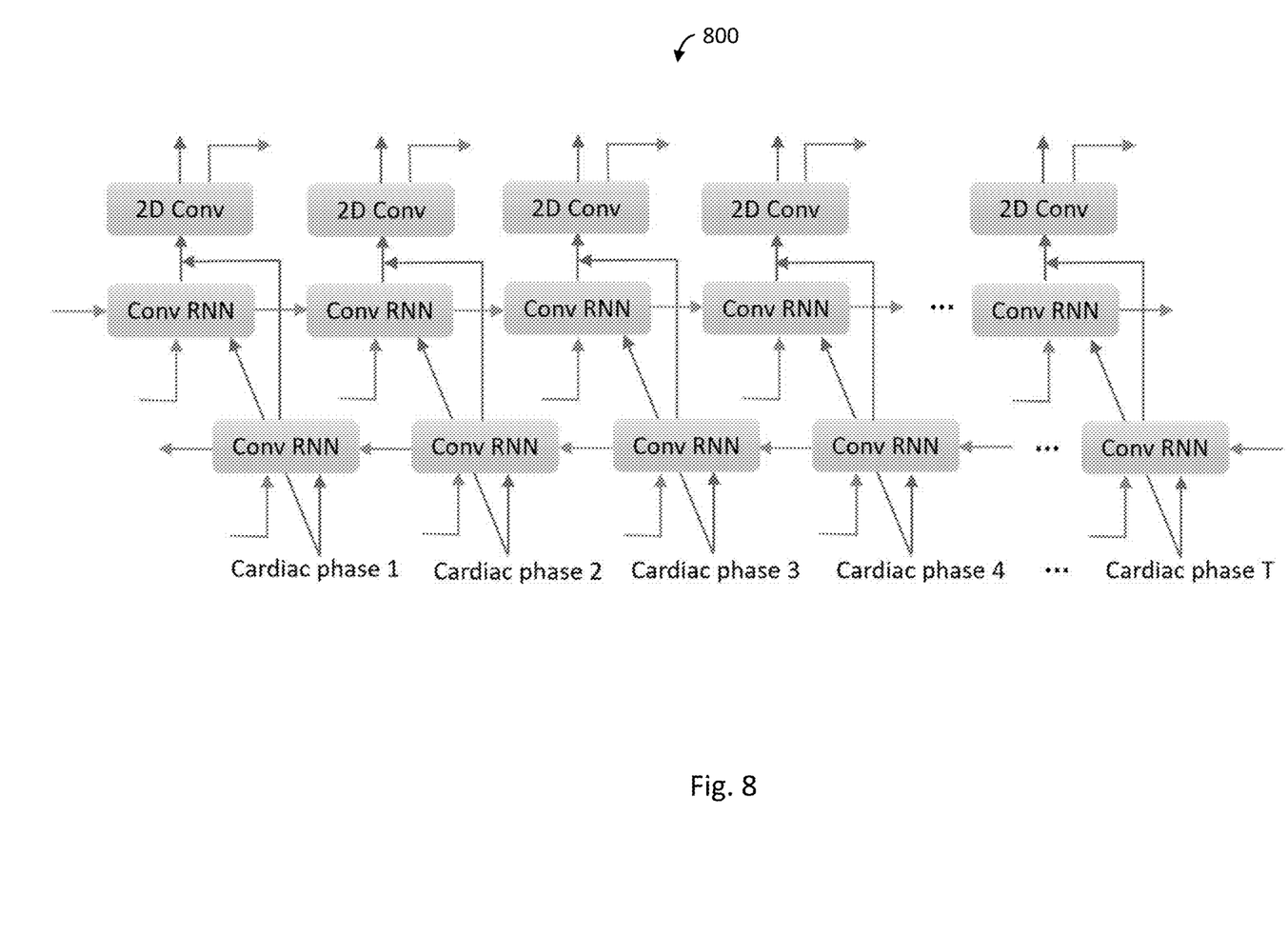
FIG. 8 illustrates an example of a bi-directional convolutional recurrent neural network cell.

FIG. 7 illustrates an example of the algorithm in the form of a deep residual convolutional recurrent neural network (Res-CRNN) 700, and FIG. 8 illustrates an example of a bi-directional convolutional recurrent neural network cell 800. One feature of the deep residual convolutional recurrent neural network is that the state neurons of a conventional recurrent neural network (RNN) may be split into a section that is responsible for the positive time direction (forward states) and a section that is responsible for the negative time direction (backward states). In addition, outputs from forward states are not connected to inputs of backward states, and outputs from backward states are not connected to inputs of forward states.

The bi-directional convolutional RNN may model the dynamic information of cardiac cine data, the data consistency layer which makes sure the reconstructed data is consistent with observed data, as well as a residual connection, which promotes the network to learn high-frequency details and adds stability to the training process. The Res-CRNN 700 may include three such building blocks $702_1$-$702_3$ and one extra residual connection $704_1$-$704_3$. The complex values are represented as a two-channel tensor and fed into the network. The deep residual convolutional recurrent neural network may be trained with the same algorithms as a regular unidirectional RNN because there are no interactions between the two types of state neurons.

As shown in FIG. 7, multi-coil subsampled real time cine data 706 from the MRI scanner 404 may be provided to the algorithm 700. Reconstructed cine images from each stage may be provided to the next stage until final reconstructed cine images 708 are achieved.

The algorithm 700 may be trained using retro-cine data and images reconstructed by the algorithm 700. Fully sampled retro-cine data may be subsampled with sampling masks similar to those used in real-time cine during MRI image acquisition. One or more of the subsampled retro-cine data, sampling masks and the fully sampled data retro cine data may also be used to train the algorithm 700. The retro-cine training data may include fully sampled images from individual coils of the MRI scanner 404. In order to conserve memory consumption, for example where the algorithm computing circuitry includes a graphics processing unit, the retrocine images may be cropped to a smaller size for training.

During training, the fully sampled retro-cine may be used to calculate loss. The training loss may be implemented in one of, or any combination of, mean square error loss, L1 loss, Structural Similarity Index (SSIM) loss, Huber loss or any loss for image quality evaluation.

Once trained, the algorithm 700 may be applied to undersampled real-time cine data for image construction, including images from multi-coil acquisitions and full size uncropped images.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method comprising:
obtaining subsampled real-time magnetic resonance imaging (MRI) data associated with multiple coils; and
reconstructing, using at least a residual convolutional recurrent neural network, the subsampled real-time MM data into a reconstructed MRI image, wherein the reconstructed MRI image reflects information acquired via the multiple coils and wherein the residual convolutional recurrent neural network comprises one or more bi-directional convolutional recurrent neural network cells.

2. The method of claim 1, wherein the subsampled real-time MRI data is based on a sub-sampling mask configured to achieve an acceleration rate of ten times or more.

3. The method of claim 2, wherein the residual convolutional recurrent neural network is trained using subsampled MRI data generated based on a sub-sampling mask that is substantially similar to the sub-sampling mask on which the subsampled real-time MRI data is based.

4. The method of claim 1, wherein the subsampled real-time MM data is acquired without electrocardiogram (ECG) gating and breath-holding, and wherein the residual convolutional recurrent neural network is trained using retro cine data acquired based on ECG gating and breath-holding.

5. The method of claim 1, wherein the residual convolutional recurrent neural network comprises one or more data consistency layers configured to ensure consistency between the reconstructed MRI image and the subsampled real-time MM data.

6. The method of claim 1, wherein the residual convolutional recurrent neural network comprises one or more residual connections configured to add high-frequency details to the reconstructed MM image.

7. The method of claim 1, wherein the residual convolutional recurrent neural network is configured to receive complex values associated with the subsampled real-time MRI data as a two-channel tensor.

8. The method of claim 1, wherein the subsampled real-time MRI data comprises respective subsampled real-time MRI data associated with multiple individual coils of an MRI wherein reconstructing the subsampled real-time MM data into the reconstructed MM image comprises:
reconstructing corresponding single-coil MM images based on the respective subsampled real-time MRI data associated with the multiple individual coils; and
generating the reconstructed MRI image based on a combination of the single-coil MM images.

9. The method of claim 8, wherein the reconstructed MRI images is generated based on a root sum of squares or one or more coil sensitivity maps associated with the multiple individual coils of the MRI scanner.

10. The method of claim 8, wherein the single-coil MM images are generated independently from each other based on the respective subsampled real-time MRI data associated with the multiple individual coils.

11. A system comprising:
computing circuitry configured to:
obtain subsampled real-time magnetic resonance imaging (MRI) data associated with multiple coils; and
reconstruct, using at least a residual convolutional recurrent neural network, the subsampled real-time MM data into a reconstructed MRI image, wherein the reconstructed MRI image reflects information acquired via the multiple coils and wherein the residual convolutional recurrent neural network comprises one or more bi-directional convolutional recurrent neural network cells.

12. The system of claim 11, wherein the subsampled real-time MRI data is based on a sub-sampling mask configured to achieve an acceleration rate of ten times or more.

13. The system of claim 12, wherein the residual convolutional recurrent neural network is trained using subsampled MM data generated based on a sub-sampling mask that is substantially similar to the sub-sampling mask on which the subsampled real-time MRI data is based.

14. The system of claim 11, wherein the subsampled real-time MRI data is acquired without electrocardiogram (ECG) gating and breath-holding, and wherein the residual convolutional recurrent neural network is trained using retro cine data acquired based on ECG gating and breath-holding.

15. The system of claim 11, wherein the residual convolutional recurrent neural network comprises one or more data consistency layers configured to ensure consistency between the reconstructed MRI image and the subsampled real-time MM data.

16. The system of claim 11, wherein the residual convolutional recurrent neural network comprises one or more residual connections configured to add high-frequency details to the reconstructed MM image.

17. The system of claim 11, wherein the residual convolutional recurrent neural network is configured to receive complex values associated with the subsampled real-time MRI data as a two-channel tensor.

18. The system of claim 11, wherein the subsampled real-time MM data comprises respective subsampled real-time MRI k-data associated with multiple individual coils of an MRI scanner and wherein the computing circuitry being configured to reconstruct the subsampled real-time MRI data into the reconstructed MRI image comprises the computing circuitry being configured to:
reconstruct corresponding single-coil MM images based on the respective subsampled real-time MRI data associated with the multiple individual coils; and
generate the reconstructed MRI image based on a combination of the single-coil MM images.

19. The system of claim 18, wherein the computing circuitry is configured to generate the reconstructed MRI images based on a root sum of squares or one or more coil sensitivity maps associated with the multiple individual coils of the MRI scanner.

20. The system of claim 18, wherein the computing circuitry is configured to generate the single-coil MM images independently from each other based on the respective subsampled real-time MM data associated with the multiple individual coils.

* * * * *